United States Patent [19]

Rosen et al.

[11] Patent Number: 5,207,658
[45] Date of Patent: May 4, 1993

[54] PRICK RESISTANT MEDICAL NEEDLE FOR INTRAVENOUS INJECTIONS

[76] Inventors: Howard J. Rosen, 6622 Horseshoe La., Huntington Beach, Calif. 92648; Mark A. Rosen, 11871 Reagen St., Los Alamitos, Calif. 90720

[21] Appl. No.: 792,253

[22] Filed: Nov. 14, 1991

[51] Int. Cl.$^5$ .............................................. A61M 5/32
[52] U.S. Cl. ................................... 604/272; 604/264
[58] Field of Search ............................... 604/272–274, 604/264; 606/222, 223

[56] References Cited

U.S. PATENT DOCUMENTS

| | | | |
|---|---|---|---|
| 3,469,579 | 9/1969 | Hubert . | |
| 3,906,932 | 9/1975 | Ayres | 604/274 X |
| 4,543,092 | 9/1985 | Mehler et al. | 604/164 |
| 4,617,019 | 10/1986 | Fecht et al. | 604/280 |
| 4,808,170 | 2/1989 | Thornton et al. | 604/274 |
| 4,958,901 | 9/1990 | Coombs | 604/44 |
| 5,064,411 | 11/1991 | Gordon | 604/48 |
| 5,100,390 | 3/1992 | Lubeck et al. | 604/158 |

FOREIGN PATENT DOCUMENTS

| | | | |
|---|---|---|---|
| 1225009 | 6/1960 | France | 604/272 |
| 0486146 | 1/1955 | Italy | 604/272 |
| 0114006 | 2/1926 | Switzerland | 604/272 |
| 9007348 | 7/1990 | World Int. Prop. O. | 604/272 |

Primary Examiner—John D. Yasko
Assistant Examiner—Adam Comak
Attorney, Agent, or Firm—Marmorek, Guttman & Rubenstein

[57] ABSTRACT

A medical intravenous injection needle which resists accidental skin pricks is disclosed. The needle tip is designed to be sharp enough to easily puncture medication bottle membranes and intravenous tubing but resists puncturing the skin. Illustratively, the tip has a flattened or rounded edge to provide the appropriate penetration ability.

15 Claims, 2 Drawing Sheets

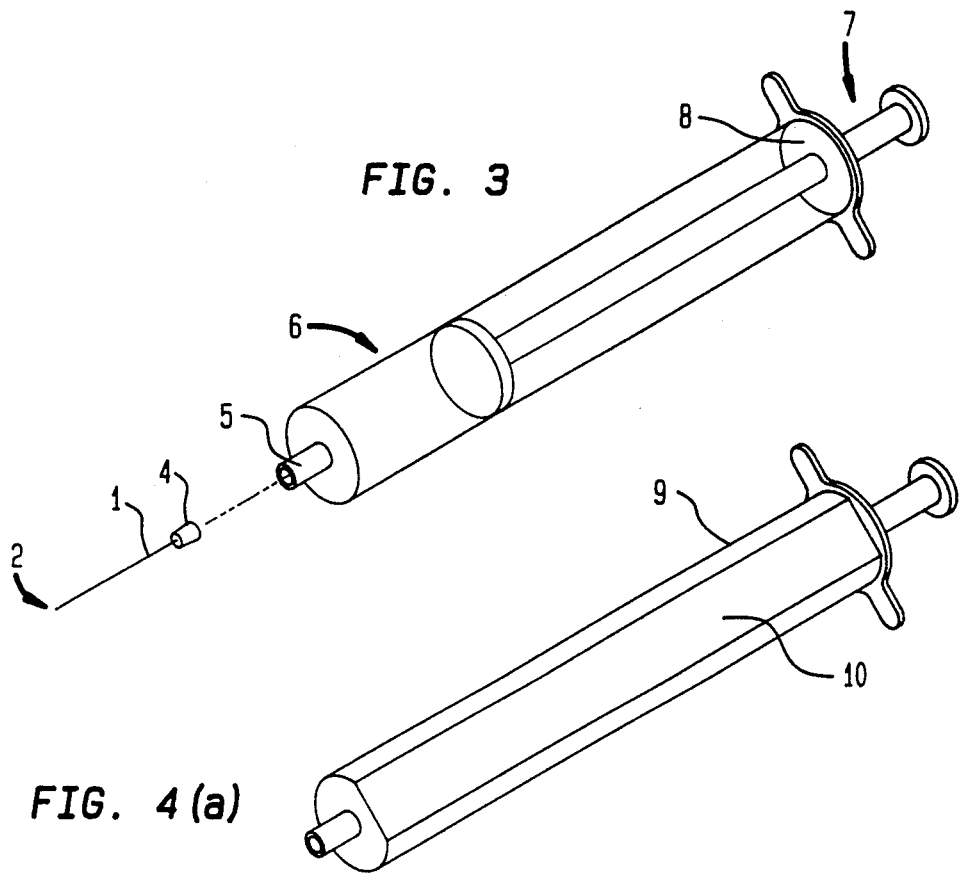
FIG. 3
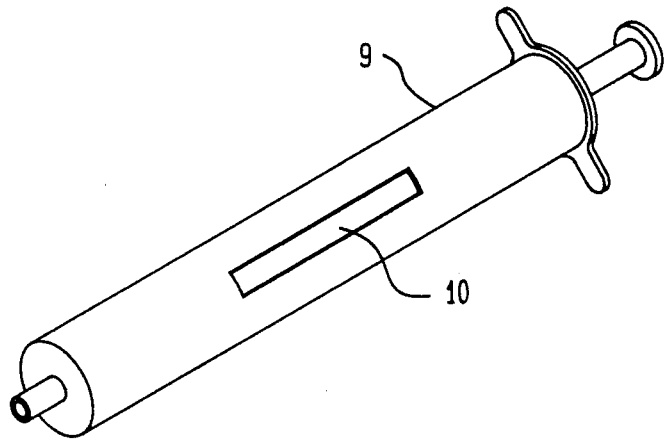
FIG. 4(a)
FIG. 4(b)
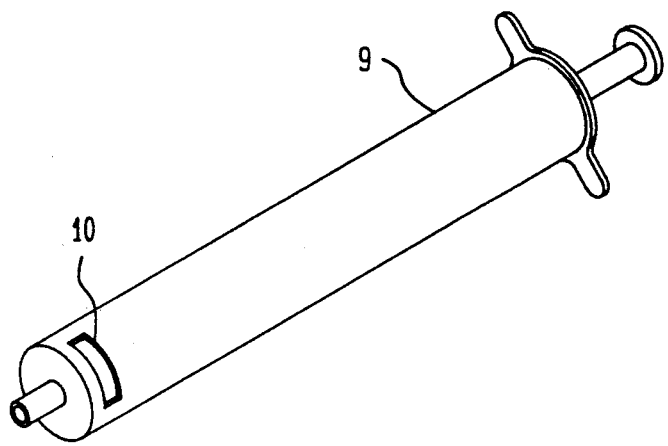
FIG. 4(c)

PRICK RESISTANT MEDICAL NEEDLE FOR INTRAVENOUS INJECTIONS

FIELD OF THE INVENTION

This invention relates to the design of prick resistant needles for use in administering drugs directly into intravenous tubing.

BACKGROUND OF THE INVENTION

In the practice of medicine, medical personnel frequently need to administer injections to patients. Occasionally, when it is desired to administer an injection to the patient, an intravenous catheter leading directly into the patient's bloodstream has already been attached. Such catheters consist of a fluid container connected to a metal or plastic needle by an IV tubing. U.S. Pat. No. 3,469,579 discloses a catheter needle and hub (which connects the needle to the catheter) made from different materials and a manner of manufacturing such an arrangement.

If the patient is already attached to an intravenous catheter then the drugs are occasionally administered directly into the intravenous tubing that leads from the fluid container directly into the patient's bloodstream (via the catheter needle). This dispenses with the need to pierce the patient's skin to administer the injection. The needles typically used for these purposes, however, were originally designed for phlebotomies. Hence, the needles are quite capable of penetrating human skin as well as the membranes of medicine bottles and intravenous tubing.

In administering injections, a phlebotomy needle comprising a sharp, slender metal or plastic tube, is attached to a hand-held syringe. While attached to the syringe, the needle is inserted into a medicine bottle covered by a membrane, and the syringe plunger retracted to draw medication into the syringe. Typically, this step is performed while holding the inverted medicine bottle with one hand and the syringe with the other hand. Once the medication has been drawn into the syringe, and air removed therefrom, the administrator typically grasps the intravenous tubing with one hand and, operating the syringe with the other hand, inserts the needle into the tubing and forces the plunger back into the syringe body to inject the medication. Thereafter, the needle is withdrawn using one hand to grasp the tubing and one hand to remove the syringe. The needle, now in a contaminated state, is typically discarded.

During all of these steps, the danger of accidental needle pricks are ever present. Accidental needle pricks by contaminated needles risk the communication of diseases carried by human blood such as AIDS or hepatitis. These risks are present even for those who administer intravenous injections as studies document that the patient's blood will move retrograde out of the patient's body and into the intravenous bottle and tubing. Thus, after an injection, the needle may be contaminated by the patient's blood and any blood diseases carried therein. Further, maintenance personnel, who come into contact with contaminated needles, may also accidentally prick themselves. Hence, it is an object of the present invention to provide a needle capable of performing intravenous injections, i.e., puncturing intravenous tubing and medicine bottle membranes, yet resistant to accidental pricking of human skin tissue.

SUMMARY

The present invention discloses a medical needle for safely administering drugs intravenously. The needle has a tip which is sharp enough to pierce the membranes of medicine bottles and intravenous tubing fairly easily yet resists the accidental puncture of human skin.

Illustratively, another embodiment of the present invention comprises a prick resistant needle with a syringe having a flattened portion formed on its outer surface. Identifying labels may be written on this flattened portion to indicate, for example, what medication is contained in the syringe. This embodiment is particularly useful in emergency room settings where prefilled syringes are kept on hand. In another embodiment, the needle is provided with a colored portion which may also be used for similar identification purposes.

BRIEF DESCRIPTION OF THE DRAWINGS

FIG. 3 shows a means of attaching the needle of FIG. 1 to a syringe.

FIGS. 4(a)-(c) show a syringe body with a flattened portion on its outer surface.

DETAILED DESCRIPTION OF THE PREFERRED EMBODIMENT

Referring to FIG. 1 a prick resistant needle 1 according to the present invention is depicted. The needle 1 is a tube normally of circular cross-section and typically ranging in size from approximately 16 to 20 gauge and about 2.5 centimeters long. The needle 1 has a tapered portion 2 which constitutes the tip of the needle.

Figure 1A:
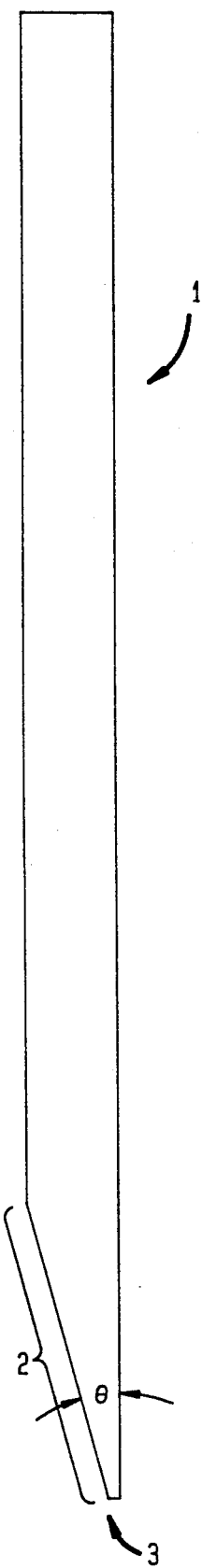
FIGS. 1(a) and 1(b) depict two side views of a needle according to the present invention.
Figure 1B:
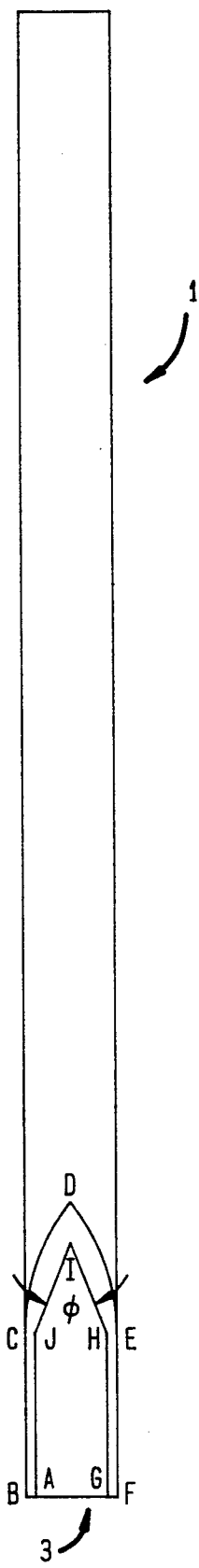

This taper may be formed by any means well known in the art. For instance, a plastic tube end may be heated and abutted into a die having a prong equal to the inner diameter of the tube attached to a base which is slanted at an angle $\theta$ to the tube axis. This would produce a tapered tip 2 as depicted in FIG. 1(a) having an opening to the tube bore on the tapered surface portion. As depicted in FIG. 1(a) the tip 2 has a triangular profile with a slanted taper along the lines defined in FIG. 1(b) by F-D or B-D. The tip 2, in this illustration, tapers at an angle 74 approximately = 14° and typically is about 4.90 millimeters along its hypotenuse and about 4.75 millimeters long along the side adjacent to the taper angle. A slot defined by letters A-B-C-D-E-F-G-H-I-J is produced by the taper 2 in the needle 1. Preferably, the slot has the following dimensions: A-B and F-G approximately = 0.1 millimeters; B-C, E-F, G-H and J-A approximately = 2 millimeters. Additionally, point D is about 4.9 millimeters, and point I about 3.1 millimeters, from the edge 3 of the tip 2. The exit port defined by A-J-I-H-G illustratively has an angle $\theta$ approximately = 30°.

The needle 1 may be manufactured from various materials such as stainless steel or plastic. As an enhancement, plastic needles may be color coded to indicate, for instance, the type of drug contained in the syringe. This embodiment is useful in a setting where prefilled syringes are kept on hand such as for emergency purposes. Further, the needles may also be attached to syringes 9 having a flattened outer surface 10 formed thereon as depicted in FIGS. 4(a)-(c) for recordation purposes. Again, this may be used to indicate the contents of syringes.

Figure 2A:
FIGS. 2(a)-(c) depict alternative needle tips according to the present invention.
Figure 2B:
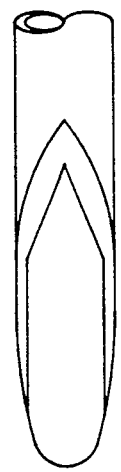
Figure 2C:

In an illustration of the invention, the tip 2 has a flattened edge 3 which is about 1 millimeter long (equal to the external width of the tube). Since the tube wall in this example, is uniformly about 0.1 millimeters thick, the edge 3 has a contact surface area of about 0.1 square millimeters. Under ordinary circumstances, this surface area provides sufficient sharpness to pierce medicine bottles and IV tubing but resists accidental skin pricks. Other tip geometries are possible according to the present invention such as semicircular tips as depicted in FIG. 2(a) or hyperbolic tips as in FIG. 2(b). The geometry may depend upon the materials used in the construction of the needle 1. For instance, a triangular tip, as depicted in FIG. 2(c) is possible for plastic needles.

As depicted in FIG. 3, a needle 1 according to the present invention illustratively has a hub 4 mounted on the end opposite its tip 2. This hub 4 has a larger outer diameter than the needle 1 and is designed for insertably mounting the needle within the inlet/outlet port 5 of a syringe 6 thereby forming a leak-proof seal. The inlet/outlet port 5 is formed on one end of the syringe 6 and a piston or plunger 7 is retractably inserted through an opening 8 in the opposite end. The plunger 7 is designed to form a vacuum seal against the inner wall of the syringe 6 so as to control the syphoning of fluid into and discharge of fluid out of the syringe 6 through the tip end passageway of the needle 1 defined by A-J-I-H-G (see FIG. 1).

In another illustration of the invention, the needle is not removable from the syringe 6. Rather, the needle 1, together with the syringe 6 form one inseparable unit. Typically, such an embodiment is formed entirely of plastic by means well known in the art and offers several advantages such as reduced assembly time under emergency circumstances.

In the operation of the invention, a sterile needle 1 is mounted onto the syringe (if necessary) by inserting the hub 4 of the needle 1 into the port 5 of a syringe 6. With the plunger 7 inserted all the way into the upright (needle up) syringe 6, a medicine bottle, having a membrane placed over its opening, is inverted and held over the needle tip 2 (the membrane prevents the fluid contained in the bottle from flowing through the bottle opening). The bottle is lowered until the needle tip 2 pierces the membrane and is in contact with the fluid. The plunger 7 is retracted, thereby drawing fluid into the syringe 6, and the needle 1 is then extracted from the membrane. Occasionally, air is removed from the syringe fluid chamber (defined by the space between the end of the plunger 7 and the port 5) prior to withdrawing the needle 1 from the bottle by inserting the plunger 7 further into the syringe 6. Since the syringe 6 is held upright, any air in the fluid chamber is above the fluid level and will be forced out of the port 5 as the plunger 7 is forced inward (thereby raising the level of the fluid in the chamber).

At this point, a portion of the IV tubing may be grasped with one hand so that the syringe needle 1 may be forced to pierce the tubing. After the needle 1 punctures the tubing, the plunger 7 may be forced back into the syringe body to discharge the fluid out of the needle tip 2 and into the tubing. Since the tubing is already directly connected to the patient's bloodstream, the fluid so introduced into the tubing enters the patient's body without the need for an additional needle prick.

After the injection, the needle 1 is contaminated and must be discarded. The needle 1 may be removed from the syringe 6 for further disposal or the syringe-needle combination may be disposed of together.

The above-mentioned embodiments are produced for illustrative purposes only. Numerous other embodiments may be produced without departing from the spirit of the present invention.

We claim:

1. A syringe needle for administering injections directly into an IV tubing comprising:
    a tube with a throughgoing bore, having a tapered tip formed on a first end thereof, said bore connecting an opening formed on said tapered tip of said tube, with an opening at a second end of said tube,
    said tapered tip having a contact surface area along which said needle may contact said IV tubing, said contact surface area of said tapered tip extending in two orthogonal directions perpendicular to a longitudinal axis of said tube, and said needle tip contact surface area being sharp enough to pierce said IV tubing but not sharp enough to pierce human skin.

2. The syringe needle of claim 1 further comprising a means for removably mounting the needle on a syringe.

3. The syringe needle of claim 2 wherein said mounting means comprises:
    an annular hub mounted co-axially on said second end of said tube having a larger outer diameter than the outer diameter of the second end and approximately equal to the inner diameter of an inlet/outlet port of a syringe for mounting the second end of the needle within said inlet/outlet port of said syringe.

4. The syringe needle of claim 1 wherein said tube is about 16–20 gauge in cross-section and about 2.5 centimeters in length, and wherein said tapered tip extends about 0.475 centimeters along the length of the tube, with said taper extending about 0.49 centimeters at an angle of about 14° with respect to said longitudinal axis.

5. The syringe needle of claim 1 wherein said tube is made of stainless steel.

6. The syringe needle of claim 1 wherein said tube is made of plastic.

7. The syringe needle of claim 1 wherein said tapered tip has a rounded edge.

8. The syringe needle of claim 1 wherein said tapered tip has a flat edge.

9. The syringe needle of claim 1 wherein said tapered tip has a pointed edge.

10. The syringe needle of claim 1 wherein said intravenous needle is color coded for identification purposes.

11. A syringe comprising:
    a cylinder for holding a fluid, said cylinder having an inlet/outlet port formed at a first end of the cylinder;
    a plunger slidably positioned in a second end of the cylinder for drawing said fluid into and discharging the fluid from the cylinder; and
    a prick resistant needle removably mounted within said inlet/outlet port of the cylinder for puncturing medicine bottle membranes and intravenous tubing comprising:
        a tube with a throughgoing bore having a tapered tip formed at a first end thereof, said bore connecting an opening formed on said tapered tip of said tube, with an opening at a second end of said tube, said tapered tip having a contact surface area along which said needle may contact said IV tubing, said contact surface area of said tapered tip extending in two orthogonal directions perpendicular to a longitudinal axis of said tube whereby said contact surface area is sharp enough to pierce intravenous tubing and medicine bottle membranes but not sharp enough to pierce human skin;

a hub mounted co-axially on said second end opposite said tip having an outer diameter larger than the second end and approximately equal to the inner diameter of the inlet/outlet port for mounting the second end of the needle within the inlet/outlet port.

12. The syringe needle of claim 11 further comprising:
a substantially flat surface formed on an outer surface of said syringe.

13. A syringe comprising:
a cylinder for holding a fluid, said cylinder having an inlet/outlet port formed at a first end of the cylinder;
a plunger slidably positioned in a second end of the cylinder for drawing said fluid into and discharging the fluid from the cylinder; and
a prick resistant needle mounted within said inlet/outlet port of the cylinder for puncturing medicine bottle membranes and intravenous tubing comprising:
a tube with a throughgoing bore, having a tapered tip formed at a first end thereof and a second end fixedly mounted within said inlet/outlet port, said bore connecting an opening formed on said tapered tip of said tube, with said inlet/outlet port,
said tapered tip having a contact surface area along which said needle may contact said IV tubing, said contact surface area of said tapered tip extending in two orthogonal directions perpendicular to a longitudinal axis of said tube whereby said contact surface area is sharp enough to pierce intravenous tubing and medicine bottle membranes but not sharp enough to pierce human skin.

14. A syringe needle for administering injections directly into an IV tubing comprising:
a cylindrical tube with a throughgoing bore extending along a longitudinal axis of said tube, having a tube wall thickness delineated by said bore and an outer surface of said tube, said tube having a tapered tip on a first end thereof, said bore connecting an opening formed at said tapered tip of said tube with an opening at a second end of said tube,
said tapered tip having a contact surface area along which said needle may contact said IV tubing, said contact surface of said needle tip, extending in a first direction orthogonal to said longitudinal axis a first distance approximately equal to said tube wall thickness and extending in a second direction orthogonal to said longitudinal axis a second distance at least equal to an outer diameter of said tube.

15. The syringe needle of claim 14 wherein said contact surface area is approximately 0.1 square millimeters.

* * * * *